United States Patent
Erman et al.

(10) Patent No.: US 7,655,816 B2
(45) Date of Patent: Feb. 2, 2010

(54) METHOD FOR STABILIZING MENTHYL LACTATE

(75) Inventors: Mark B. Erman, Atlantic Beach, FL (US); Joe W. Snow, Kingsland, GA (US)

(73) Assignee: Millennium Specialty Chemicals, Houston, TX (US)

( * ) Notice: Subject to any disclaimer, the term of this patent is extended or adjusted under 35 U.S.C. 154(b) by 14 days.

(21) Appl. No.: 12/079,824

(22) Filed: Mar. 28, 2008

(65) Prior Publication Data

US 2008/0262260 A1   Oct. 23, 2008

Related U.S. Application Data

(63) Continuation of application No. 11/787,830, filed on Apr. 18, 2007, now Pat. No. 7,381,834.

(51) Int. Cl.
*C07C 69/66* (2006.01)
(52) U.S. Cl. .................................... 560/188; 560/179
(58) Field of Classification Search .................. None
See application file for complete search history.

(56) References Cited

U.S. PATENT DOCUMENTS 5,783,725 A * 7/1998 Kuhn et al. ................. 560/188
7,173,146 B1   2/2007 Erman et al. ................ 560/188
2006/0165783 A1   7/2006 Korber ....................... 424/464

OTHER PUBLICATIONS

Ojima, et al., "Reduction of Carbonyl Compounds via Hydrosilylation. 3. Asymmetric Reduction of Keto Esters via Hydrosilylation Catalyzed by a Rhodium Complex with Chiral Phosphine Ligands", *Journal of Organic Chemistry*, 42(10), 1977 pp. 1671-1679.
Boireau, et al., "Highly Diastereoselective Reduction of (−) methylphenylglyoxalate and (—) menthylpyruvate Using New Hindered Lithiumtrialkoxyaluminohydrides", *Tetrahedron: Asymmetry*, vol. 2(8), pp. 771-774, 1991.

* cited by examiner

*Primary Examiner*—Karl J Puttlitz
(74) *Attorney, Agent, or Firm*—Jonathan L. Schuchardt

(57) ABSTRACT

A method for stabilizing menthyl lactate is disclosed. The method comprises combining water with a solution comprising menthyl lactate and a water-miscible organic solvent in amounts effective to precipitate menthyl lactate from the resulting aqueous mixture. The aqueous precipitation method is simple to practice, and it provides menthyl lactate having remarkably improved storage stability.

6 Claims, No Drawings and# METHOD FOR STABILIZING MENTHYL LACTATE

CROSS-REFERENCE TO RELATED APPLICATION

This application is a continuation of application Ser. No. 11/787,830, filed Apr. 18, 2007 now U.S. Pat. No. 7,381,834.

FIELD OF THE INVENTION

The invention relates to menthyl lactate, a commonly used physiological coolant. In particular, the invention relates to a way to improve the storage stability of menthyl lactate.

BACKGROUND OF THE INVENTION

Menthyl lactate (ML) is used in many consumer products for which a long-lasting physiological cooling effect is desired. Such products include comestibles, toiletries, pharmaceuticals, and cosmetics. Pure ML has a faint, minty odor and is practically tasteless.

Despite its popularity in consumer products, menthyl lactate lacks adequate storage stability. ML is commercially available as a solidified distillate or as a crystalline product. Upon storage, usually within weeks, the melting point drops significantly, the product develops an acidic, pungent odor, and the ML consequently becomes unusable for most intended applications. Moreover, the solid product is often melted several times before its incorporation in the consumer product. This "thermal loading" further reduces quality, which is frequently accompanied by a rise in acid number.

U.S. Pat. No. 5,783,725 teaches to prevent the acidic, pungent note by stabilizing ML with an alkali metal and/or alkaline earth metal carbonate and/or bicarbonate, which can be added during crystallization. Normally, the crystallization is performed in an organic solvent (e.g., acetone) in the presence of the inorganic salt (see Example, col. 2, ll. 29-41). Stabilizing ML with the inorganic salt overcomes the need to formulate immediately after purchase. However, the mixture of ML and inorganic salt obtainable by this method has its own drawbacks, particularly when the salt is less compatible than ML with other components used to make the consumer product. The inorganic salt can confound formulators by triggering undesirable and often unpredictable phase separation.

U.S. Pat. Appl. Publ. No. 2006/0165783 teaches that menthyl lactate with improved stability can be obtained by compacting solid (flaked or crystalline) ML, typically under 30-80 kN of force, into pellets, spheres, or other geometric forms. Such high-pressure equipment is preferably avoided, however. Moreover, compacted ML is less convenient to use compared with, for example, crystals or a free-flowing powder.

U.S. Pat. No. 7,173,146 teaches a process for making menthyl lactate. Menthol and lactic acid react in the presence of a base to make ML and higher lactoyl esters of ML, followed by controlled hydrolysis to convert the higher lactoyl esters back to ML. The reference teaches that the "esterified product containing ML and higher lactoyl esters can be purified, if desired, by any suitable means, including distillation, crystallization, or the like, but it is preferably used 'as is' for the next step, which involves controlled hydrolysis" (see col. 4., ll. 16-23). The '146 patent later teaches that after hydrolysis, the "ML product can be purified by any suitable method, including, for example, distillation, crystallization, precipitation, sublimation, or a combination thereof. Distillation is preferred" (col. 5, ll. 19-26). All of the examples of the '146 patent defer purification until after controlled hydrolysis, and all of the examples use vacuum distillation to purify the ML. Thus, the '146 patent teaches a variety of purification schemes, with distillation preferred, and fails to disclose the specific combination of water and a solution of ML in a water-miscible organic solvent to precipitate ML. Moreover, nothing in the reference suggests the desirability of using aqueous precipitation instead of, e.g., distillation or crystallization, to enhance the stability of ML.

In sum, a need remains for a way to make menthyl lactate having improved storage stability. Preferably, the method would provide an easy-to-handle powder or crystalline ML rather than large pellets or compacted material and would avoid the need for high-pressure equipment. A valuable method would improve ML stability without the need for the inorganic salt stabilizers that can interfere with compatibility. An ideal method would be easy to practice with conventional equipment and reagents.

SUMMARY OF THE INVENTION

The invention relates to a method for stabilizing menthyl lactate. The method comprises combining water with a solution comprising menthyl lactate and a water-miscible organic solvent in amounts effective to precipitate menthyl lactate from the resulting aqueous mixture.

Although previously unexplored, aqueous precipitation is simple, and we surprisingly found that it provides menthyl lactate having remarkably improved stability compared with that of an unprecipitated sample. In particular, menthyl lactate stabilized by precipitation normally has—and retains even after prolonged storage—improved physical properties that may include a high melting point, good color and dimensional stability, a low acid number, high GC purity, and a faint, minty odor.

DETAILED DESCRIPTION OF THE INVENTION

Menthyl lactate suitable for use in the method of the invention can be from any desired source. The product is commercially available from various suppliers, including Symrise (as Frescolat® ML), or it can be synthesized, usually from lactic acid and menthol, according to well-known methods. Suitable methods for making ML are described in U.S. Pat. No. 7,173,146, the teachings of which are incorporated herein by reference, and references cited therein.

As used herein, "menthyl lactate" includes all possible stereoisomers and isomer mixtures. Suitable menthyl lactate derives from any combination of any of the eight possible stereoisomers of menthol with any combination of either of the two possible stereoisomers of lactic acid. Thus, the menthol used could be, for example, l-menthol, d-menthol, dl-menthol (i.e., a racemic mixture of l-menthol and d-menthol), isomers of neomenthol, isomenthol, or neoisomenthol, or mixtures thereof. Because it provides ML having excellent physiological cooling properties, l-menthol is particularly preferred. Either L-(+)-lactic acid or D-(−)-lactic acid can be reacted with the menthol to make ML. Lactic acid is commonly supplied as a concentrated solution in water (e.g., 85+ wt. % lactic acid). An example is HS-88 solution, a product of Purac, which contains about 88 wt. % of lactic acid in water. Suitable lactic acid includes L-(+)-lactic acid, D-(−)-lactic acid, the racemic mixture (i.e., DL-lactic acid), and mixtures thereof. Because it provides ML having excellent physiological cooling properties, L-(+)-lactic acid is particularly preferred. Thus, among many other possibilities, the menthyl lactate might contain predominantly l-menthyl-L-lactate, which is the preferred product obtained by reacting l-menthol and L-(+)-lactic acid. Alternatively, it might contain d-menthyl, neomenthyl, and isomenthyl L- and D-lactates in optically pure and/or racemic forms.

The invention relates to a way to impart substantial storage stability to menthyl lactate. We unexpectedly found that the stability of ML can be dramatically improved by combining water with a solution of ML in a water-miscible organic solvent in amounts effective to precipitate ML from the resulting aqueous mixture. The method provides high yields of ML as a powder or fine crystals with excellent storage stability.

A water-miscible organic solvent is used to make a solution containing menthyl lactate. The concentration of ML in the water-miscible organic solvent can vary over a broad range, from saturated or nearly saturated solutions to dilute ones, but a reasonable amount of organic solvent is normally used. The solution preferably contains from 10 wt. % to an amount of ML that saturates the solution. Preferably, the solution contains from 10 to 70 wt. %, more preferably from 15 to 65 wt. %, and most preferably from 25 to 65 wt. % of ML. The solubility limit of ML in the water-miscible organic solvent will depend on the identity of the solvent and, to a limited degree, on the particular ML stereoisomer mixture and its purity level.

Suitable water-miscible organic solvents are at least highly soluble if not completely miscible with water. They include lower aliphatic alcohols (methanol, ethanol, 1-propanol, isopropanol), ketones (acetone), glycols (ethylene glycol, propylene glycol), glycerin, dimethylformamide, carboxylic acids (formic acid, acetic acid, aqueous lactic acid), ethers (1,2-dimethoxyethane), and the like, and mixtures thereof. Particularly preferred water-miscible organic solvents, because of their availability, low-cost, and ease-of-use, are acetone and lower alcohols. The solution comprising menthyl lactate and the water-miscible organic solvent can include other components. Preferably, however, the solution contains only ML and the water-miscible organic solvent.

Water is combined with the menthyl lactate solution in an amount effective to precipitate ML from the resulting aqueous mixture. Preferably, pure water used, but an aqueous phase containing minor amounts of acids, bases, salts, or water-miscible organic solvent might also be used to precipitate the ML. The volume ratio of water to water-miscible organic solvent in the resulting aqueous mixture can vary over a wide range and depends on the particular choice of solvent, ML concentration, temperature, the desired particle size, and other factors. The volume ratio is preferably within the range of 1:20 to 40:1, more preferably within the range of 1:10 to 20:1, and most preferably within the range of 1:5 to 10:1. If too little water is added, precipitation of the ML may be incomplete; with too much water, however, the ML is more difficult to recover and a larger amount of wastewater is generated.

The precipitation can be performed over a wide temperature range. Preferably, however, it is performed at a temperature within the range of −10° C. to 40° C., more preferably from −5° C. to 20° C., and most preferably from −5° C. to 5° C.

The manner of combining the water and the menthyl lactate solution is not critical. In one approach, the precipitation is effected by adding water to the ML solution. Alternatively, the ML solution can be added to water. Moreover, precipitation can be achieved batchwise or continuously, e.g., by mixing the ML solution and water in a mixing tube.

In one aspect of the invention, the solution of menthyl lactate in the water-miscible organic solvent is obtained by simply dissolving fused, melted, or crystalline ML in the appropriate solvent. In another aspect, the ML is first synthesized by esterifying lactic acid with menthol in a water-miscible solvent. The resulting solution is then used for the precipitation. When the ML is synthesized in this way, the water-miscible organic solvent preferably contains no hydroxyl groups that might interfere with the esterification reaction. Thus, preferred water-miscible organic solvents for this approach include, for example, glyme (1,2-dimethoxyethane), diglyme, and the like.

After precipitation, the menthyl lactate is normally separated from the aqueous mixture by conventional methods, for example, filtration, centrifugation, decantation, or the like, and is optionally dried, also by conventional methods.

Precipitation according to the method of the invention provides menthyl lactate having improved stability compared with that of an unprecipitated sample. By "improved stability," we mean that one or more important physical properties of the menthyl lactate becomes more constant as a function of time as a consequence of precipitation when compared with menthyl lactate that has not been precipitated according to the method. Important physical properties include, without limitation, appearance, dimensional stability, color, texture, organoleptic properties (odor, flavor), melting point, acid number, GC purity, optical rotation, pH, solubility, and the like. Preferably, the ML retains its desirable physical property or properties even after prolonged storage. "Prolonged" depends on the particular application, but it is preferably at least one week, more preferably at least one month, and most preferably at least one year.

Preferred menthyl lactate obtained by the method of the invention retains at least one, and preferably all, of the following properties for at least one month, more preferably for at least one year: (1) melting point: >43.5° C.; (2) GC purity: >99.5%; (3) acid number: <0.2 mg KOH/g; (4) odor: faint, minty; not acidic or pungent; (5) appearance: white, crystals or powder.

Interestingly, other well-known ways to purify menthyl lactate do not provide high yields of ML having the enhanced stability available from practicing the method of the invention. For example, simple crystallization of ML from acetone gives a product whose physical properties (dimensional stability, odor, melting point, GC purity, acid number) deteriorate over the course of several months (see Comparative Example 3, below). Crystallization from isopropanol or other lower alcohols provides ML with improved stability, but the results are not as good as those obtained by precipitation (Comparative Example 4). In contrast, aqueous precipitation can provide ML that retains high quality, even after years of storage (Example 1). Importantly, the yield of ML from water precipitation is far superior to that obtained by simple crystallization.

The invention includes menthyl lactate produced by the method of the invention. While menthyl lactate produced according to the method of the invention meets published specifications for commercial ML, menthyl lactate of the invention differs in having markedly enhanced shelf stability. The enhanced stability is evidence that the precipitated ML of the invention differs compositionally from commercial material in a way that is not easily identified by ordinary analytical means.

Menthyl lactate produced by the method of the invention is valuable for many traditional ML applications including, for example, comestible items such as chewing gum, chewing tobacco, cigarettes, ice cream, confectionery and drinks, as well as in toiletries and pharmaceutical or cosmetic preparations such as dentifrices, mouthwashes, perfumes, powders, lotions, ointments, oils, creams, sunscreens, shaving creams and aftershaves, shower gels or shampoos. In most or all of these applications, improved ML stability should have a positive impact on overall product quality.

The following examples merely illustrate the invention. Those skilled in the art will recognize many variations that are within the spirit of the invention and scope of the claims.

EXAMPLE 1

Precipitation of Menthyl Lactate from Isopropanol

A sample of solid menthyl lactate (110 g, ~98% pure) is dissolved in isopropanol (60 g). This 65 wt. % solution is added with stirring over about 2 h to water (1000 g) at 3° C. The mixture stirs for 15 min. and is filtered. The product is air dried overnight to give menthyl lactate (107 g, 97%) as a fine, white crystalline powder. M.p.: 43.7° C.; purity: 99.8% by gas chromatography (GC); acid number: 0.15 mg KOH/g.

After storage for 39 months in a closed glass jar, the product is evaluated for quality. Appearance: fine, white crystalline powder; m.p.: 43.9° C.; GC purity: 99.8+%; acid number: 0.15 mg KOH/g; odor: faint, minty; approved by an expert panel.

Conclusion: menthyl lactate stabilized by the method of the invention retains its high quality even after prolonged storage.

COMPARATIVE EXAMPLE 2

Storage of Unprecipitated Menthyl Lactate

A sample of solid menthyl lactate from the same batch that was used in Example 1 is stored under similar conditions for the same 39 months. The sample develops a strong, pungent acidic odor. Mp: 39.3° C.; GC purity: <96%; acid number: 32 mg KOH/g.

Conclusion: ML quality deteriorates upon prolonged storage in the absence of aqueous precipitation according to the method of the invention.

COMPARATIVE EXAMPLE 3

Crystallization from Acetone

A sample of solid menthyl lactate (222 g) from the same batch is dissolved in acetone (112 g) and is crystallized from this solution by lowering the temperature to 0° C. The crystals are quickly isolated by filtration and air dried overnight (99.8 g, 45%) to provide a white, crystalline powder. M.p.: 43.6° C.; GC purity 99+%; acid number: 0.13 mg KOH/g.

After storage for 39 months, the product shrinks and acquires a strong, pungent acidic odor. M.p.: 36.7° C.; GC purity: 92%; acid number: 20 mg KOH/g.

Conclusion: crystallizing ML from acetone alone will not impart storage stability; moreover, the yield of ML is low compared with the amount obtained using the aqueous precipitation method of the invention.

COMPARATIVE EXAMPLE 4

Crystallization from Isopropanol

A sample of solid menthyl lactate (48 g) from the same batch is dissolved in isopropanol (52 g) and is crystallized from this solution by lowering the temperature to −5° C. The crystals are quickly isolated by filtration and air dried overnight. Yield of white, crystalline powder: 11 g (23%). M.p.: 44.0° C.; GC purity: 99+%; acid number: 0.13 mg KOH/g.

After storage for 39 months, some deterioration of odor quality is observed. M.p.: 43.6° C.; acid number: 0.27 mg KOH/g.

Conclusion: although the decrease in quality of ML crystallized from isopropanol is minor, the yield is low compared with the amount obtained using the aqueous precipitation method of the invention.

COMPARATIVE EXAMPLE 5

Crystallization from Heptane

A sample of solid menthyl lactate (50 g) from the same batch is dissolved in heptane (50 g) and is crystallized from this solution by lowering the temperature to −5° C. The crystals are quickly isolated by filtration and air dried overnight. Yield of white, crystalline powder: 27 g (55%). M.p. 44.1° C.; GC purity: 100%; acid number: 0.06 mg KOH/g.

After storage for 39 months, the product acquires a strong, pungent acidic odor. M.p.: 43.7° C.; GC purity: 97%; acid number: 0.32 mg KOH/g.

Conclusion: crystallizing ML from heptane alone will not impart storage stability; moreover, the yield of ML is low compared with the amount obtained using the aqueous precipitation method of the invention.

EXAMPLE 6

Precipitation from Isopropanol

A sample of solid menthyl lactate (100 g) is dissolved in isopropanol (50 g). This 67% solution is added over about 20 min. to water (1000 g) at 5-9° C. The mixture stirs for 30 min. and is then filtered. The product is air dried overnight to a white, crystalline powder. Yield: 92 g (92%); m.p.: 44.4° C.; GC purity: 99.9%; acid number: 0.09 mg KOH/g.

EXAMPLE 7

Precipitation from Isopropanol

A sample of solid menthyl lactate (43 g) is dissolved in isopropanol (100 g). This 30% solution is added over about 20 min. to water (2000 g) at 5-9° C. The mixture stirs for 30 min. and is then filtered. The product is air dried overnight to a white, crystalline powder. Yield: 38 g (88%); m.p.: 44.4° C.; GC purity: 100%; acid number: 0.06 mg KOH/g.

EXAMPLE 8

Precipitation from Ethanol

A sample of solid menthyl lactate (100 g) is dissolved in ethanol (50 g). This 67% solution is added over about 20 min. to water (1000 g) at 5-9° C. The mixture stirs for 1 h and is then filtered. The product is air dried overnight to a white, crystalline powder. Yield: 90 g (90%); m.p.: 44.1° C.; GC purity: 100%; acid number: 0.06 mg KOH/g.

EXAMPLE 9

Precipitation from Ethanol

A sample of solid menthyl lactate (43 g) is dissolved in ethanol (100 g). This 30% solution is added over about 20 min. to water (2000 g) at 5-9° C. The mixture stirs for 1 h and is then filtered. The product is air dried overnight to a white, crystalline powder. Yield: 39 g (91%); m.p.: 43.8° C.; GC purity: 99.9%; acid number: 0.06 mg KOH/g.

EXAMPLE 10

Precipitation from Acetone

A sample of solid menthyl lactate (100 g) is dissolved in acetone (50 g). This 67% solution is added over about 20 min. to water (1000 g) at 5-9° C. The mixture stirs for 30 min. and is then filtered. The product is air dried overnight to a white, crystalline powder. Yield: 92 g (92%); m.p.: 43.9° C.; GC purity: 99.8%; acid number: 0.13 mg KOH/g.

EXAMPLE 11

Precipitation from Acetone

A sample of solid menthyl lactate (43 g) is dissolved in acetone (100 g). This 30% solution is added over about 20 min. to water (2000 g) at 5-9° C. The mixture stirs for 30 min. and is then filtered. The product is air dried overnight to a white, crystalline powder. Yield: 36 g (83%); m.p.: 43.9° C.; GC purity: 99.9%; acid number: 0.15 mg KOH/g.

The examples are meant only as illustrations. The following claims define the invention.

We claim:

1. Menthyl lactate solid composition obtained by a method which consists of combining water with a solution consisting of menthyl lactate and a water-miscible organic solvent in amounts effective to precipitate menthyl lactate from the resulting aqueous mixture, wherein the precipitation provides menthyl lactate having improved stability compared with that of an unprecipitated sample.

2. Menthyl lactate of claim 1 that retains a melting point greater than 43.5° C. after storage for at least one week.

3. Menthyl lactate of claim 1 that retains a GC purity greater than 99.5% after storage for at least one week.

4. Menthyl lactate of claim 1 that retains an acid number less than 0.2 mg KOH/g after storage for at least one week.

5. Menthyl lactate of claim 1 that retains a faint, minty odor after storage for at least one week.

6. Menthyl lactate of claim 1 that is isolated from the aqueous mixture as a powder or crystals.

* * * * *